United States Patent
Whayne et al.

[11] Patent Number: 6,113,591
[45] Date of Patent: *Sep. 5, 2000

[54] SYSTEMS AND METHODS FOR SENSING SUB-SURFACE TEMPERATURES IN BODY TISSUE

[75] Inventors: James G. Whayne, Saratoga; David K. Swanson, Mountain View; Sidney D. Fleischman, Menlo Park; Thomas M. Bourne, Mountain View; Dorin Panescu, Sunnyvale, all of Calif.

[73] Assignee: EP Technologies, Inc., San Jose, Calif.

[ * ] Notice: This patent is subject to a terminal disclaimer.

[21] Appl. No.: 08/942,251

[22] Filed: Oct. 1, 1997

Related U.S. Application Data

[63] Continuation of application No. 08/431,907, May 1, 1995, which is a continuation-in-part of application No. 08/266,023, Jun. 27, 1994.

[51] Int. Cl.$^7$ .................................................. A61B 17/36
[52] U.S. Cl. .............................. 606/34; 606/40; 606/50; 606/51
[58] Field of Search ......................... 606/31–52

[56] References Cited

U.S. PATENT DOCUMENTS

| | | |
|---|---|---|
| 4,860,744 | 8/1989 | Johnson et al. . |
| 4,950,267 | 8/1990 | Ishihara et al. ........................... 606/15 |
| 5,073,167 | 12/1991 | Carr et al. . |
| 5,330,518 | 7/1994 | Neilson et al. . |
| 5,334,193 | 8/1994 | Nardella . |
| 5,348,554 | 9/1994 | Imran et al. . |
| 5,383,876 | 1/1995 | Nardella . |
| 5,423,811 | 6/1995 | Imran et al. . |
| 5,431,649 | 7/1995 | Mulier et al. . |
| 5,456,682 | 10/1995 | Edwards et al. . |
| 5,480,417 | 1/1996 | Hascoet et al. . |
| 5,688,267 | 11/1997 | Panescu et al. ........................... 606/31 |
| 5,702,386 | 12/1997 | Stern et al. ............................... 606/42 |
| 5,735,846 | 4/1998 | Panescu et al. ........................... 606/42 |
| 5,743,903 | 4/1998 | Stern et al. ............................... 606/42 |
| 5,755,715 | 5/1998 | Stern et al. ............................... 606/42 |
| 5,797,905 | 8/1998 | Fleischmann et al. .................... 606/41 |
| 5,800,432 | 9/1998 | Swanson ................................... 606/41 |
| 5,853,409 | 12/1998 | Swanson et al. ......................... 606/42 |

FOREIGN PATENT DOCUMENTS

| | | | |
|---|---|---|---|
| 9315664 | 8/1993 | WIPO ..................................... 606/49 |
| WO 94/10922 | 5/1994 | WIPO ............................ A61B 17/36 |

*Primary Examiner*—David M. Shay
*Attorney, Agent, or Firm*—Lyon & Lyon LLP

[57] ABSTRACT

Systems and methods supply ablation energy to an electrode in contact with tissue to form a tissue-electrode interface. The system and methods sense, simultaneously with ablation, at least two tissue temperature conditions using at least two tissue temperature sensing elements which are held within a carrier that is substantially isolated from thermal conductive contact with the electrode. The carrier holds the tissue temperature sensing elements in a spaced apart relationship in thermal conductive contact with tissue at different depths beneath the tissue-electrode interface. The systems and methods control the supply of ablation energy to the electrode based, at least in part, upon temperatures sensed by the tissue temperature sensing elements.

15 Claims, 8 Drawing Sheets

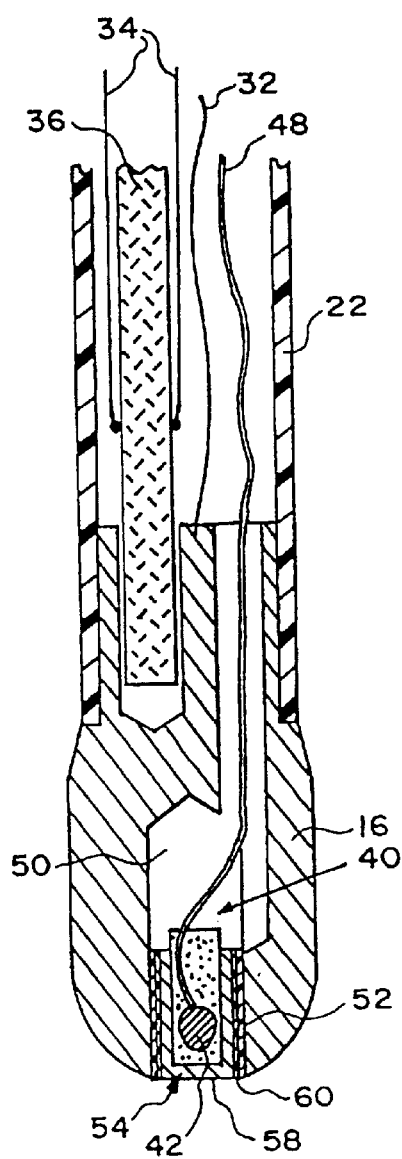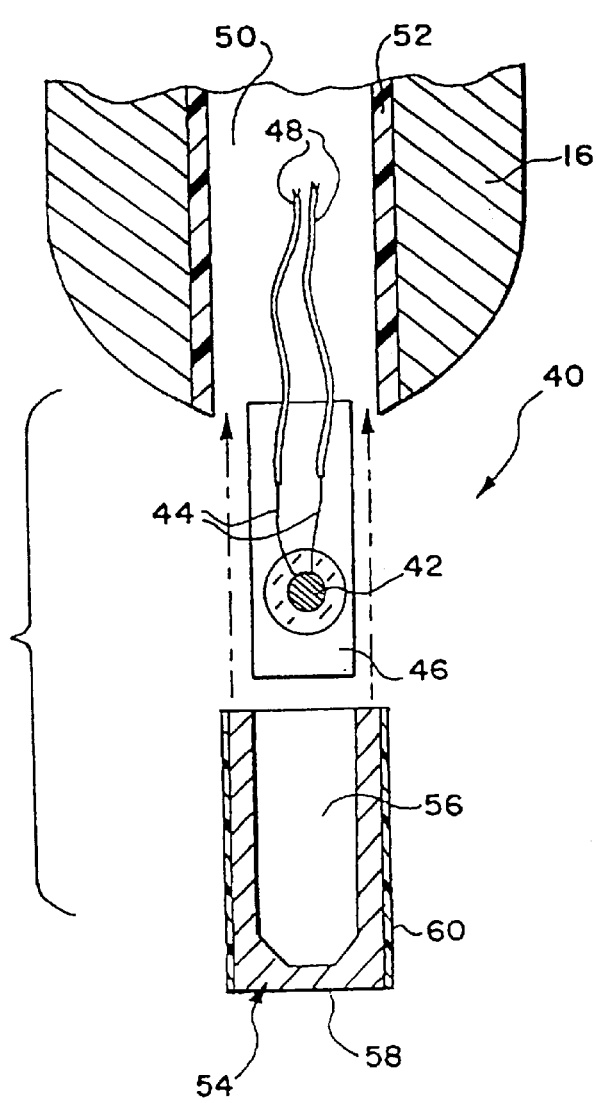
FIG. 2
FIG. 3

FIG. 4
FIG. 5
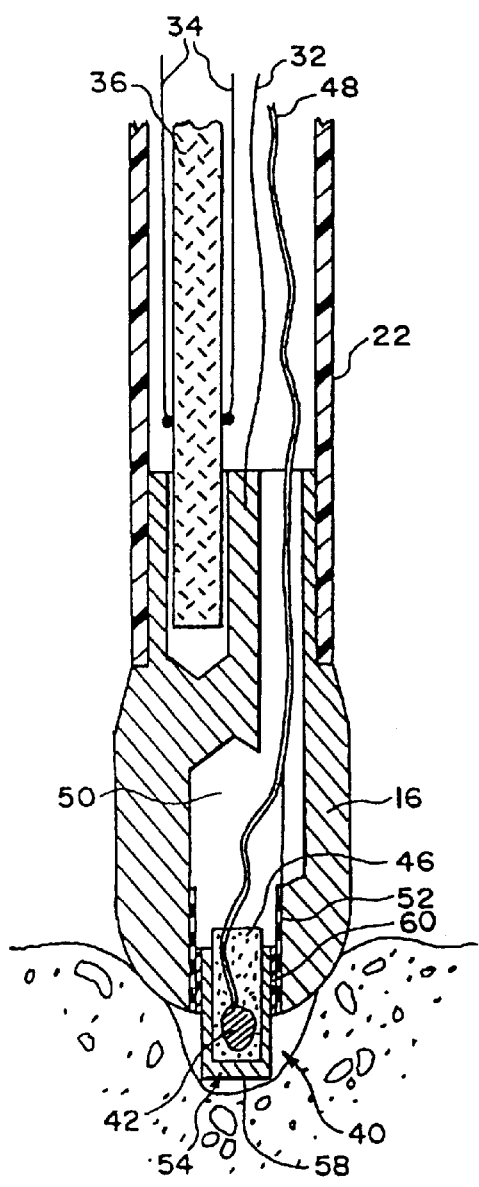
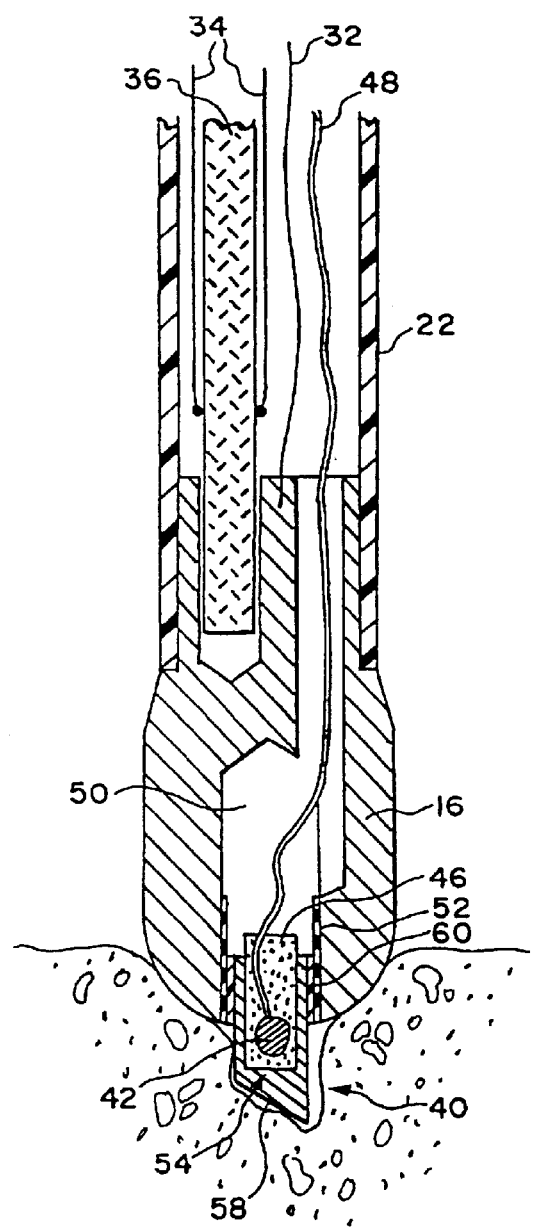

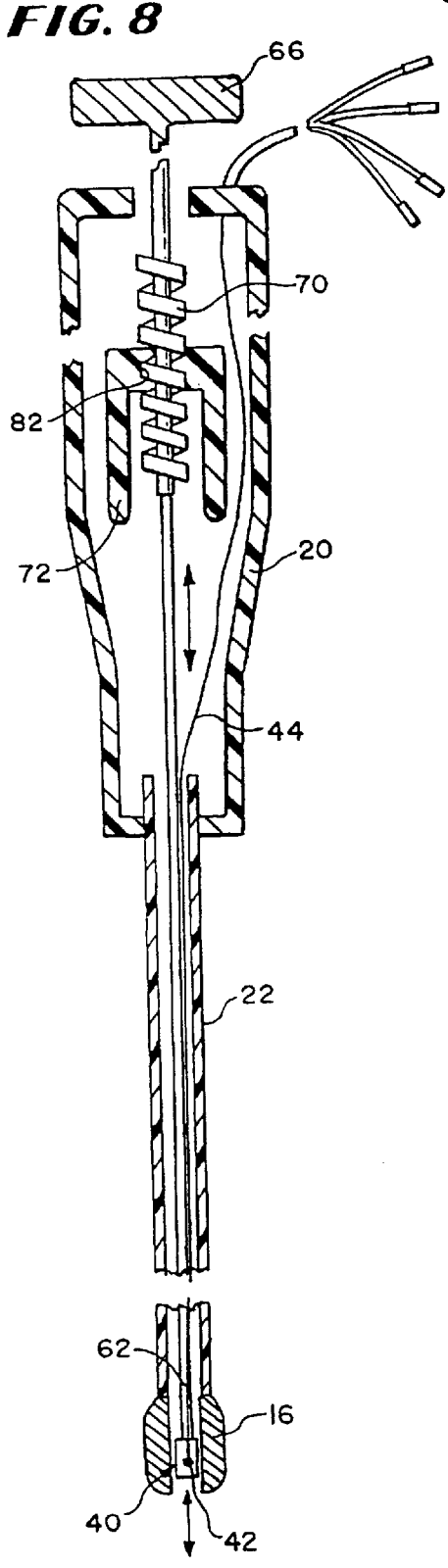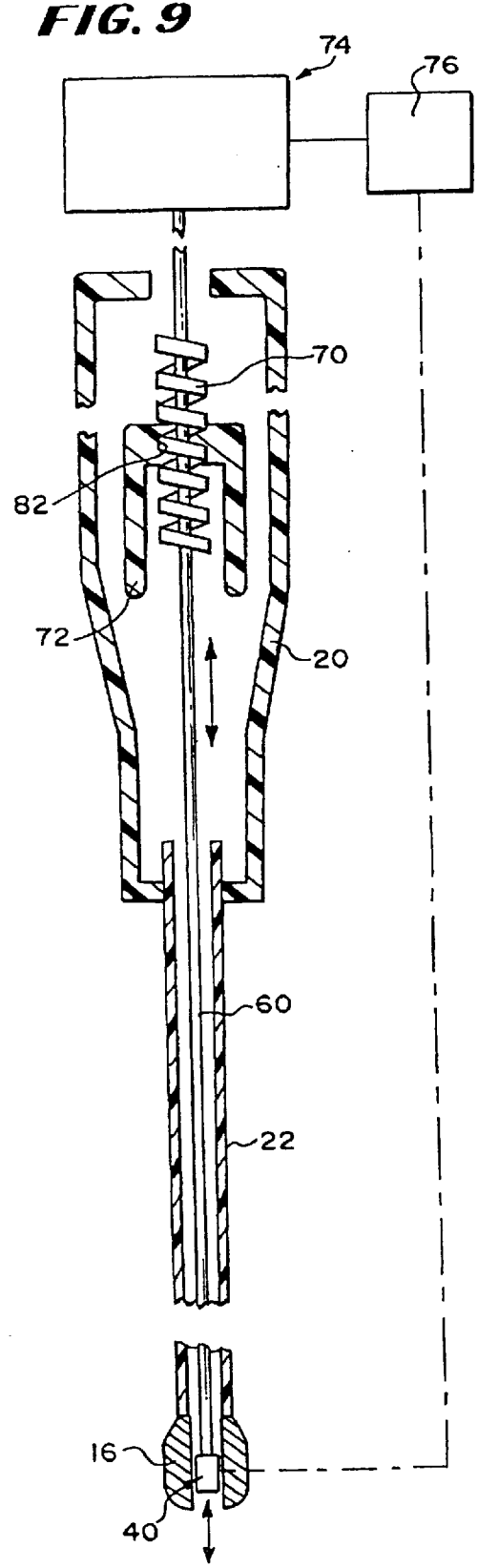

FIG. 12
FIG. 14
FIG. 13
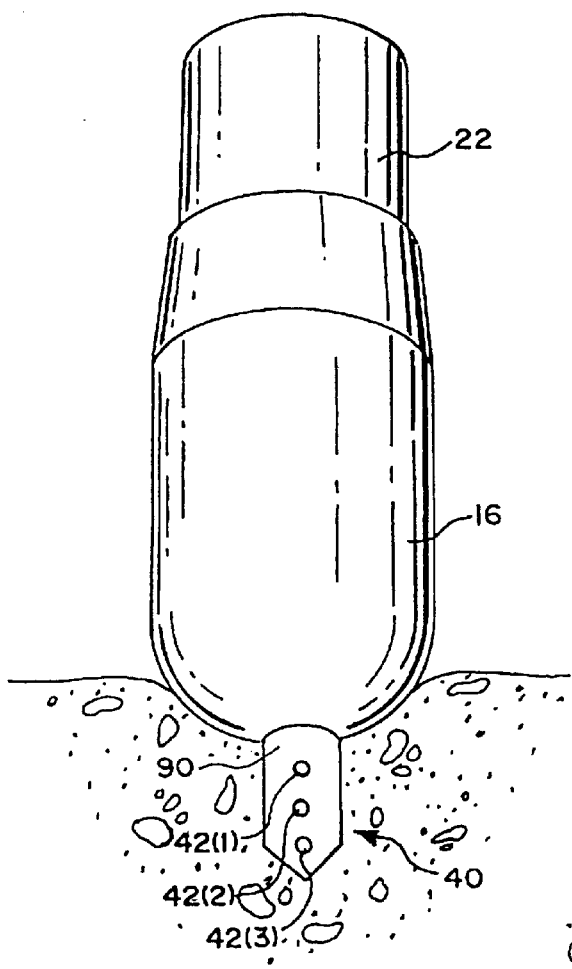
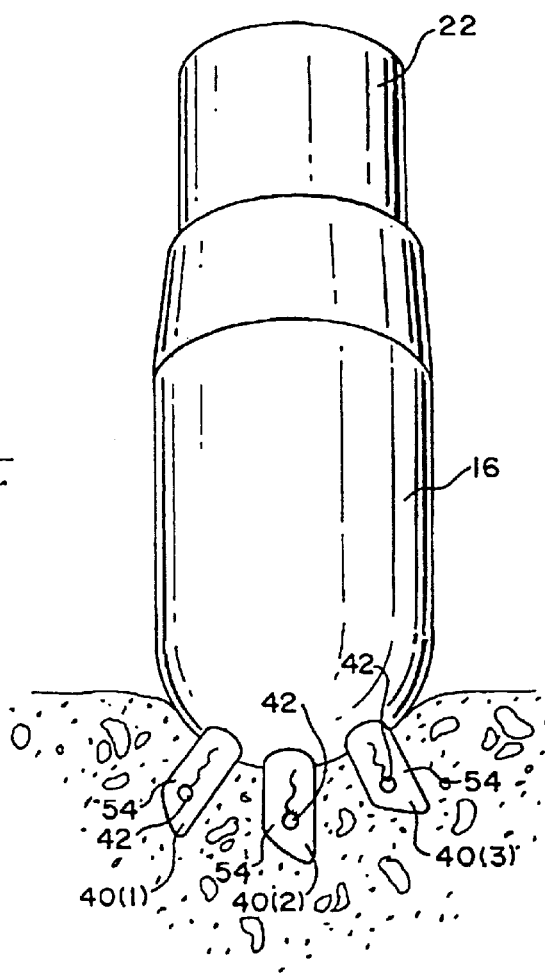
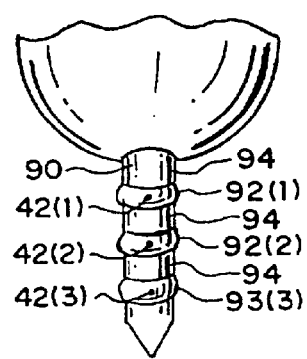

SYSTEMS AND METHODS FOR SENSING SUB-SURFACE TEMPERATURES IN BODY TISSUE

This is a continuation of copending application Ser. No. 08/431,907 filed on May 1, 1995; which is a continuation-in-part of application Ser. No. 08/266,023 filed Jun. 27, 1994.

FIELD OF THE INVENTION

In a general sense, the invention is directed to systems and methods for creating lesions in the interior regions of the human body. In a more particular sense, the invention is directed to systems and methods for ablating heart tissue for treating cardiac conditions.

BACKGROUND OF THE INVENTION

Physicians frequently make use of catheters today in medical procedures to gain access into interior regions of the body. In some procedures, the catheter carries an energy transmitting element, which is typically a metal electrode, on its distal tip to ablate body tissues.

In such procedures, the physician must establish stable and uniform contact between the energy transmitting element and the tissue to be ablated. Upon establishing contact, the physician must then carefully apply ablating energy to the element for transmission to the tissue.

The need for precise control over the emission of ablating energy is especially critical during catheter-based procedures for ablating heart tissue. These procedures, called electrophysiology therapy, are becoming increasingly more widespread for treating cardiac rhythm disturbances, called arrhythmias. Cardiac ablation procedures typically use radio frequency (RF) energy to form a lesion in heart tissue.

The level of ablating energy can be controlled, at least in part, by using a temperature sensing element to monitor surface tissue temperatures during ablation. Because of the particular heat exchange conditions between the tissue and the metallic ablation electrode contacting it, the surface temperatures measured by the sensing element usually will not correspond with the actual maximum tissue temperature. This is because the region of hottest temperature occurs beneath the surface of the tissue, usually at a depth of about 0.5 to 1.0 mm from where the energy transmitting electrode (and the sensing element) contacts the tissue. If the power is applied to heat the tissue too quickly, the actual maximum tissue temperature in this sub-surface tissue region may exceed 100° C., while the surface tissue temperature sensed by the temperature sensor is only 80° C. Sub-surface micro explosions are the unintended results.

The principal objective of the invention is to provide systems and methods for monitoring and reliably controlling the application of energy to ablate body tissue, thereby providing therapeutic results in a consistent and predictable fashion.

SUMMARY OF THE INVENTION

The invention provides systems and methods that provide reliable control over tissue heating and ablation procedures using temperature sensing. According to the invention, the systems and methods control the application of energy to an energy transmitting electrode using power adjustments that take into account sub-surface temperature conditions.

One aspect of the invention provides systems and methods for ablating body tissue. The systems and methods include an ablation element for contacting tissue at an interface. The ablation element is adapted to be connected to a source of ablation energy to conduct ablation energy for transmission by the element into tissue at the interface. The systems and methods also include at least two tissue temperature sensing elements held in a carrier in a spaced apart relationship in thermal conductive contact with tissue at different depths beneath the interface. The spaced tissue temperature sensing elements allow the physician to obtain and monitor a spatial map of sub-surface temperature conditions.

Another aspect of the invention provides systems and methods for ablating body tissue by supplying ablation energy to an electrode in contact with tissue to form a tissue-electrode interface. The system and methods sense, simultaneously with ablation, at least two tissue temperature conditions using at least two tissue temperature sensing elements which are held within a carrier that is substantially isolated from thermal conductive contact with the electrode. The carrier holds the tissue temperature sensing elements in a spaced apart relationship in thermal conductive contact with tissue at different depths beneath the tissue-electrode interface. The systems and methods control the supply of ablation energy to the electrode based, at least in part, upon temperatures sensed by the tissue temperature sensing elements.

Other features and advantages of the inventions are set forth in the following Description and Drawings, as well as in the appended claims.

BRIEF DESCRIPTION OF THE DRAWINGS

FIG. 2 is a side section view of an energy transmitting electrode that can be associated with the system shown in FIG. 1, showing a fixed temperature sensing element carried within a heat conducting cap by the electrode for sensing surface tissue temperature;

FIG. 3 is an exploded side view of the temperature sensing element shown in FIG. 2;

FIG. 4 is a side section view of another energy transmitting electrode that can be associated with the system shown in FIG. 1, showing a outward projecting, blunt end temperature sensing element carried within a heat conducting cap by the electrode for sensing tissue temperature below the tissue surface;

FIG. 5 is a side section view of another energy transmitting electrode that can be associated with the system shown in FIG. 1, showing a outward projecting, pointed end temperature sensing element carried within a heat conducting cap by the electrode for sensing tissue temperature below the tissue surface;

FIG. 8 is a section view of a manually rotatable stylet used to incrementally adjust the position of the movable temperature sensing element shown in FIGS. 6 and 7;

FIG. 9 is a section view of an automatically incrementally movable stylet with temperature sensing feedback control loop that can be used to adjust the position of the movable temperature sensing element shown in FIGS. 6 and 7;

FIG. 12 is an enlarged end view of an energy transmitting electrode carrying an outward projecting temperature sensing element with multiple temperature sensors for sensing multiple sub-surface tissue temperatures;

FIG. 13 is an enlarged end view of a housing establishing thermal conductive contact between tissue and multiple temperature sensors below the tissue surface using spaced regions of thermal conductive material substantially isolated from thermal conductive contact with each other; and FIG. 14 is an enlarged end view of an energy transmitting electrode carrying multiple temperature sensing elements, each sensing element projecting into tissue to sense sub-surface tissue temperature.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 1:
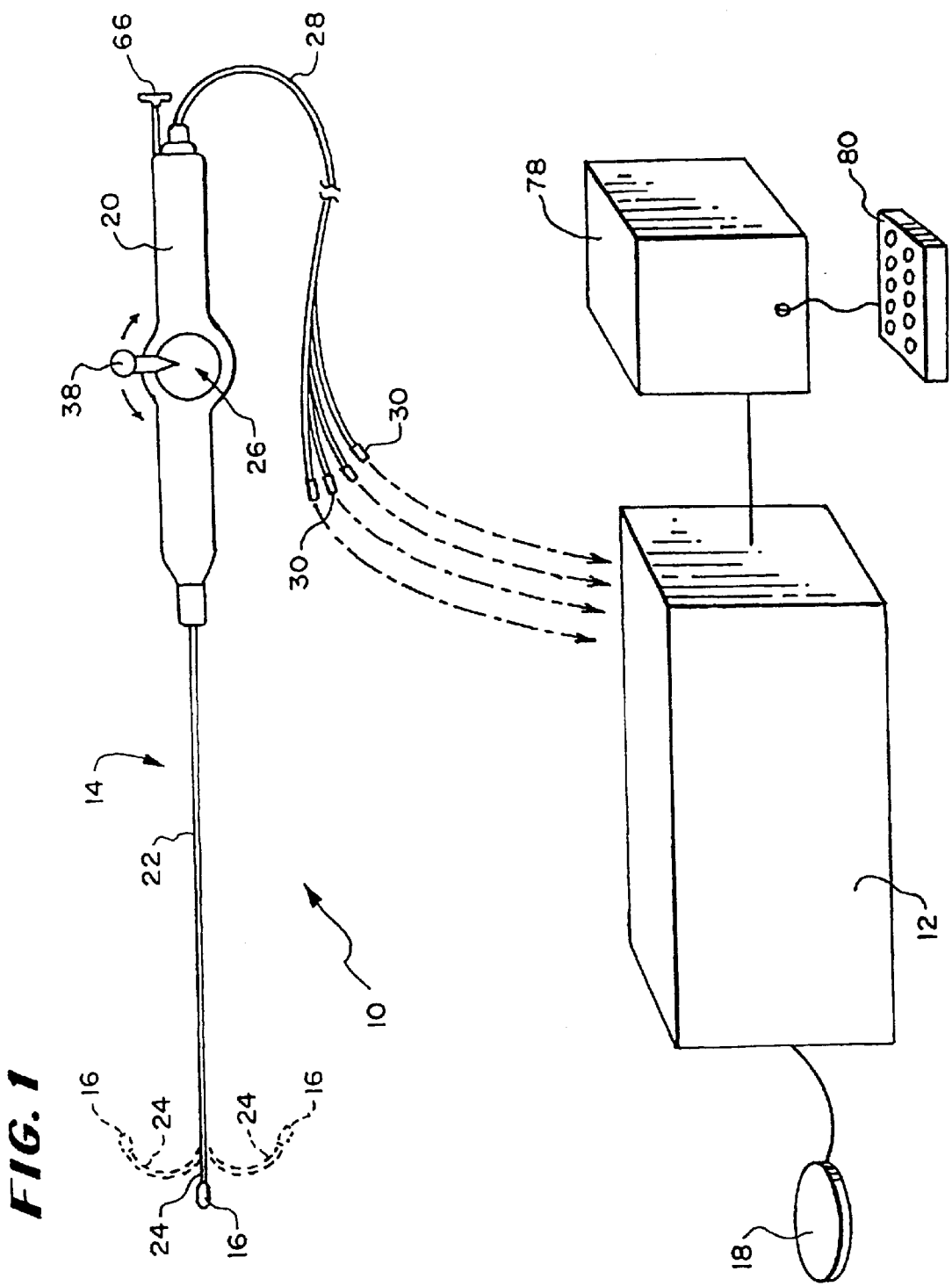
FIG. 1 shows a system for ablating tissue that embodies the features of the invention.

FIG. 1 shows a system 10 for ablating human tissue that embodies the features of the invention.

In the illustrated and preferred embodiment, the system 10 includes a generator 12 that delivers radio frequency energy to ablate tissue. Of course, other types of energy can be generated for tissue ablating purposes.

The system 10 also includes a steerable catheter 14 carrying a radio frequency transmitting ablation electrode 16. In the illustrated embodiment, the ablation electrode 16 is made of platinum/iridium. The ablation electrode 16 can be made from other energy transmitting materials like, for example, stainless steel, gold, or silver alloys.

In the illustrated embodiment, the system 10 operates in a unipolar mode. In this arrangement, the system 10 includes a patch electrode that serves as an indifferent electrode 18. In use, the indifferent electrode 18 attaches to the patient's back or other exterior skin area.

Alternatively, the system 10 can be operated in a bipolar mode. In this mode, the catheter 14 carries both electrodes.

The system 10 can be used in many different environments. This specification describes the system 10 when used to provide cardiac ablation therapy.

When used for this purpose, a physician steers the catheter 14 through a main vein or artery (typically the femoral vein or artery) into the interior region of the heart that is to be treated. The physician then further manipulates the catheter 14 to place the electrode 16 into contact with the tissue within the heart that is targeted for ablation. The user directs radio frequency energy from the generator 12 into the electrode 16 to ablate and form a lesion on the contacted tissue.

I. The Ablation Catheter

In the embodiment shown in FIG. 1, the catheter 14 includes a handle 20, a flexible catheter body 22, and a catheter distal section 24, which carries the electrode 16.

The handle 20 encloses a steering mechanism 26 for the catheter distal section 24. A cable 28 extending from the rear of the handle 20 has plugs 30. Some of the plugs 30 are coupled to a signal wire 32 (see FIG. 2) that extends from the ablation electrode 16 through the catheter body 22. The plugs 30 connect to the generator 12 for conveying radio frequency energy to the ablation electrode 16 through the wire 32.

Left and right steering wires 34 (also see FIG. 2) extend through the catheter body 22 to interconnect the steering mechanism 26 in the handle 20 to the left and right sides of a deflecting spring element 36. Rotating a steering lever 38 on the handle to the left causes the steering mechanism 26 to pull on the left steering wire, causing the spring element 36 to bend to the left (as shown in phantom lines in FIG. 1). Similarly, rotating the steering lever 38 to the right causes the steering mechanism 26 to pull on the right steering wire 34, causing the spring element 36 to bend to the right (as also shown in phantom lines in FIG. 1). In this way, the physician steers the ablation electrode 16 into contact with the tissue to be ablated.

Further details of this and other types of steering mechanisms for the ablating element 10 are shown in Lundquist and Thompson U.S. Pat. No. 5,254,088, which is incorporated into this Specification by reference.

A. Temperature Sensing

As FIGS. 2 and 3 show, the ablation electrode 16 carries at least one temperature sensing element 40. As will be described in greater detail later, the power that the generator 12 applies to the electrode 16 is set, at least in part, by the temperature conditions sensed by the element 40.

In the embodiment illustrated in FIGS. 2 and 3, the temperature sensing element 40 comprises a conventional small bead thermistor 42 with one or more associated lead wires 44. In a preferred implementation, the thermistor 42 comprises a 0.55 mm bead thermistor commercially available from Thermometrics (Edison, N.J.), Part Number AB6B2-GC16KA143E/37° C-A.

It should be appreciated that other types of temperature sensing elements can also be used. For example, a thermocouple could be used as the temperature sensing element. In a preferred implementation, the thermocouples are constructed by either spot welding or by laser stripping and welding the different metals together to form the thermocouple junction. When a thermocouple serves as the temperature sensing element, a reference thermocouple must be used. The reference thermocouple may be placed in the handle 20 or exposed to the blood pool in the manner disclosed in copending U.S. patent application Ser. No. 08/286,937, filed Aug. 8, 1994, and entitled "Systems and Methods for Sensing Temperature Within the Body."

Potting compound 46 encapsulates the thermistor 42 and adjacent lead wires 44. Insulating sheaths 48 also shield the lead wires 44 outside the potting compound 46. Together, the compound 46 and sheaths 48 electrically insulate the thermistor 42 from the surrounding ablation electrode 16.

The potting compound 46 and insulation sheathes 48 can be made with various materials. In the illustrated embodiment, heavy isomid serves as the potting compound 46, although another cyanoacrylate adhesive, a silicon rubber RTV adhesive, polyurethane, epoxy, or the like could be used. The sheaths 48 are made from polyamide material, although other conventional electrical insulating materials also can be used.

Similar electrical insulation is required when thermocouples are used as the temperature sensors. For example, the thermocouple junction can be placed in a thermally conducting epoxy inside a polyester sleeve. In a preferred implementation, the thermocouple junction is placed in silicon rubber RTV adhesive (NuSil Technologies, Carpenteria, Calif.) within a shrink polyester sleeve, which is then shrunk to fit tightly about the thermocouple junction and wires. To reduce electrical interference, the thermocouple wires are also preferably shielded and twisted together.

Figure 7:
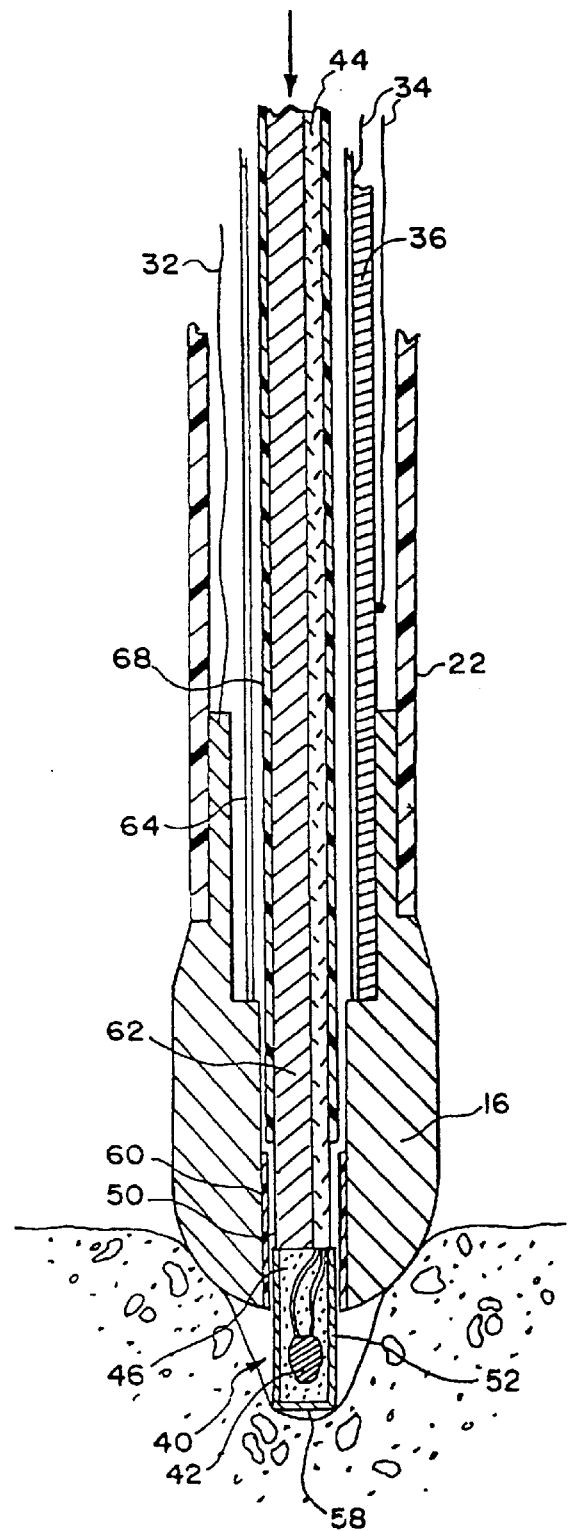
FIG. 7 is a side section view of the energy transmitting electrode shown in FIG. 6, showing the movable temperature sensing element in its extended position projecting into tissue.

As FIGS. 7 and 8 best show, the lead wires 44 for the thermistor 42 extend through the catheter body 22 and into the catheter handle 20. There, the lead wires 44 electrically couple to the cable 28 extending from the handle 20. The cable 28 connects to the generator 12, transmitting temperature signals from the thermistor 42 to the generator 12.

The temperature sensing element 40 can be located on the ablation element 16 in various ways, depending upon where the physician desires to sense temperature conditions. In the embodiment shown in FIGS. 2 and 3, the sensing element 40 is arranged to sense temperature conditions on the surface of endocardial tissue the electrode 16 contacts. In the alternative embodiments shown in FIGS. 4 to 11, the sensing element 40 is arranged to sense temperature conditions below the surface of endocardial tissue the electrode 16 contacts.

1. Surface Temperature Sensing

In the embodiment illustrated in FIGS. 2 and 3, the ablation electrode 16 includes an interior well 50. The temperature sensing element 40 occupies a portion of the well 50 to make thermal conductive contact with the surface of endocardial tissue.

In the embodiment shown in FIGS. 2 and 3, a thermal insulating tube 52 lines the interior wall of the well 50 adjacent to the temperature sensing element 40. The thermal insulation tube 52 can, for example, be adhesively bonded to the interior wall of the well 50.

The thermal insulating material of the tube 52 can vary. In the illustrated embodiment, it is a polyamide material having a wall thickness of about 0.003 inch. Other thermal insulating materials like Mylar or kapton could be used.

The thermal insulating tube 52 thermally insulates the temperature sensing element 40 from the thermal mass of the electrode 16. In this way, the temperature condition sensed by the sensing element 40 more closely represents the actual tissue temperature condition at the surface of the endocardium, which the sensing element 40 contacts. Also, the thermally insulated sensing element 40 is less affected by variations in the temperature of the electrode 16 itself, which can vary significantly due to changes in tissue contact and the complex cooling effects of the blood pool circulating about the electrode 16 during use.

Still, it has been determined that, even when the sensing element 40 is thermally insulated from the thermal mass of the electrode 16, the sensed temperature may be at least four times more sensitive to the temperature of the electrode 16 than to temperature of the tissue. The preferred embodiment shown in FIGS. 2 and 3 therefore provides improved sensitivity to tissue temperature by surrounding the sensing element 40 with a surface 54 that is essentially isothermal with the temperature of the tissue it contacts.

More particularly, the surface 54 comprises a material having a high thermal conductivity that is at least 1.0 watt (W) per meter (m) Kelvin (K), or 1.0 W/m K. Metallic materials like stainless steel, aluminum, gold, silver alloy, platinum, copper, and compositions containing stainless steel, aluminum, gold, silver, and platinum possess this degree of thermal conductivity. For example, stainless steel has a thermal conductivity of about 15 W/m K, and platinum has a thermal conductivity of about 71 W/m K. This thermal conductivity is significantly higher than the thermal conductivity of potting material 46 surrounding the thermistor 40. For example, silicon rubber has a thermal conductivity of only about 0.13 W/m K, and polyurethane has a thermal conductivity of only about 0.026 W/m K.

In the illustrated and preferred embodiment (see FIG. 3), the surface 54 is formed as a carrier or cap having an open interior 56. The encapsulated thermistor 42 snugly occupies the cap interior 56 in thermal conductive contact with the cap 54. Preferably, the thermistor 42 is potted within the open interior using an epoxy having an enhanced thermal conductivity that is at least 1.0 W/m K. The inclusion of a metallic paste (for example, containing aluminum oxide) in a standard epoxy material will provide this enhanced thermal conductivity. When the ablation energy is radio frequency energy, the potting material must also electrically insulate the temperature sensing element 40 from the cap 54.

The cap 54 in turn is fitted within the well 50 of the electrode 16. The cap 54 has a distal end 58 that extends beyond the length of the encapsulated thermistor 42 to make thermal conductive contact with tissue. The high thermal conductivity of the cap 54 assures that it will rapidly reach an equilibrium temperature close to that of tissue it contacts.

In the illustrated and preferred embodiment, a thermal and electrically insulating barrier 60 forms an interface between the side of the cap 54 and the interior wall of the well 50. The barrier 60 (together with the tube 52) thermally insulates the cap 54 from the surrounding thermal mass of the electrode 16. The barrier 60 also electrically insulates the cap 54 from the electrode 16.

In a preferred implementation (see FIG. 3), the cap 54 is made from stainless steel 304 (having a thermal conductivity of about 15 W/m K). The cap 54 has a wall thickness along the sidewall and at the distal end of about 0.005 inch. The cap 54 has an overall length of about 0.060 inch and an overall width of about 0.033 inch (the open interior being about 0.022 inch in width). The encapsulated thermistor 42 is fixed to the cap interior 56 using a thermally conducting epoxy like EP42HTAO (Master Bond, Inc., Hackensack, N.J.). The thermal conductivity of this epoxy (which includes aluminum oxide) is about 1.15 W/m K. The barrier 60 comprises polyamide adhered about the sidewall of the cap 54 using cyanoacrylate FMD-14 to serve as an electrical insulator. The barrier 60 also comprises polyester shrink tubing secured by heat shrinking about the polyamide to serve as a thermal insulator. The complete assembly is then potted within the electrode well using cyanoacrylate FMD-13 (Loctite Corporation, Newington, Conn.).

EXAMPLE

The thermal sensitivity of a temperature sensing element enclosed in a thermally conductive carrier according to the invention (Sensor 1) was compared to the thermal sensitivity of a temperature sensing element free of the carrier (Sensor 2).

Sensor 1 was carried within the well of an 8 F diameter/4 mm long standard platinum/iridium radio frequency transmitting electrode. Sensor 1 comprised a 0.55 mm bead thermistor embedded in a glass bead, which in turn was embedded in an epoxy resin, which was encapsulated in a polyamide sheath. The entire encapsulated thermistor assembly was mounted by FMD-14 within a cap, as above described, made of stainless steel 304 having a wall thickness of 0.005 inch. The exterior side walls of the cap were thermally isolated from the electrode by one layer of polyamide and one layer of polyester shrink tubing. The assembly was potted within the electrode well using FMD-13. The distal tip of the cap was free of thermal insulating material and was flush with the distal tip of the electrode for contact with tissue.

Sensor 2 comprised a thermocouple potted with solder in thermal conductive contact within an 8 F/4 mm standard platinum/iridium radio frequency transmitting electrode.

The thermal sensitivity of each Sensor 1 and 2 was tested by placing the consolidated electrode and sensor assembly into a water bath maintained at 20° C. A soldering wand maintained at a temperature of 60° C. was placed into contact with each electrode beneath the surface of the water. This contact was maintained to achieve steady state conditions both against the side of the electrode (the electrode being held horizontally) and at the distal tip of the electrode (the electrode being held vertically). The temperatures sensed by each Sensors 1 and 2 in both electrode orientations were recorded.

The following Table summarizes the results:

TABLE

Comparison of the Thermal Sensitivity of Temperature Sensor Carried Within a Thermal Conductive Surface to the Thermal Sensitivity of Temperature Sensor Without a Thermal Conductive Surface

|  | VERTICAL POSITION | HORIZONTAL POSITION |
| --- | --- | --- |
| SENSOR 1 (With Thermal Conductive Surface) | 59° C. | 40° C. |
| SENSOR 2 (Without Thermal Conductive Surface) | 40° C. | 39° C. |

The above Table shows that Sensor 2 is not sensitive to the actual temperature of the 60° C. heat source. Regardless of its orientation, Sensor 2 continues to sense the 40° C. temperature of the thermal mass of the electrode itself (the remainder of the heat energy of the source being dissipated by the surrounding water bath).

In contrast, Sensor 1 shows significant sensitivity with respect to its contact orientation with the 60° C. heat source. When held horizontally, out of direct contact with the heat source, Sensor 2, like Sensor 1, senses the 40° C. temperature of the thermal mass of the electrode itself. However, when held vertically, in direct contact with the heat source, Sensor 1 essentially senses the actual temperature of the heat source, and not the temperature of the electrode. The cap encapsulating Sensor 1, having a high intrinsic thermal conductivity of at least 1.0 W/m K, directly conducts heat from the source for sensing by Sensor 1. The thermal conducting cap creates an isothermal condition about Sensor 1 close to the actual temperature of the source. Furthermore, the cap, being substantially isolated from thermal conductive contact with the electrode, retains this isothermal condition about Sensor 1, preventing its dissipation by the thermal mass of the electrode.

In quantitative terms, the 59° C. temperature sensed by Sensor 1 when in direct contact with the 60° C. heat source, compared to the 46° C. electrode temperature sensed when not in direct contact with the source, accounts for 19 of the total 20 units of actual temperature difference between the heat source and the electrode. Thus, in quantitative terms, the presence of the thermal conducting cap in Sensor 1 establishes a 95% sensitivity to the temperature of the heat source (i.e., which, in use, would be sensitivity to actual tissue temperature), and only a 5% sensitivity to the temperature of the electrode itself. This is compared to an essentially 100% sensitivity of Sensor 2 to the temperature of the electrode. In the absence of the cap that embodies the invention, Sensor 2 is virtually insensitive to the actual temperature of the heat source (i.e., actual tissue temperature).

(ii) Sub-Surface Temperature Sensing

Since the highest tissue temperature conditions develop during ablation beneath the surface of the endocardium, it is desirable to locate one or more temperature sensing elements 40 to sense sub-surface temperature conditions.

In the embodiment illustrated in FIGS. 4 and 5, the ablation electrode 16 includes the interior well 50 at its tip end, like that previously disclosed. The temperature sensing element 40 occupies this well 50. Unlike the previously described embodiment, the sensing element 40 shown in FIGS. 4 and 5 is potted in position within the well 50 so as to extend beyond the tip of the electrode 16. At least a portion of the sensing element 40 thus projects beneath the surface of the endocardium that the electrode 16 contacts. The sensing element 40 is thereby positioned to sense sub-surface tissue temperature conditions.

In the illustrated and preferred embodiment, the sub-surface temperature sensing element 40 takes the form of an encapsulated thermistor 42, as already described. Still, it should be appreciated that other types of temperature sensing elements, like thermocouples, could be used for sub-surface temperature sensing according to the invention.

Also, in the illustrated and preferred embodiment, the sub-surface temperature sensing element 40 is enclosed within the thermally conducting cap 54, as already described. As before explained, the cap 54 provides enhanced thermal conducting characteristics, creating an isothermal surface around the sub-surface sensor 40 quickly achieving thermal equilibrium with the surrounding tissue temperature conditions. The cap 54 also provides added strength to resist bending or fracture during manufacturing and handling.

In the illustrated and preferred embodiment, the cap 54 is also electrically and thermally insulated from the electrode 16 by the barrier 60 and sleeve 52, which line the wall of the well 50 that the sensor 40 occupies. As before explained, the barrier 60 and sleeve 52 prevent thermal and electrical interference with the temperature sensor 42. Ohmic heating of the cap 54 is prevented so as not to interfere with temperature readings, or so that localized damage or charring to tissue contacting the cap 54 is prevented.

In the embodiment shown in FIG. 4, the distal cap end 58 presents a blunt surface that projects from the end of the electrode 16, but does not actually penetrate tissue. The endocardium is malleable enough to conform about the electrode and the projecting cap 54. In the embodiment shown in FIG. 5, the cap end 58 presents a sharpened surface that actually penetrates into the endocardium. By causing the cap 54 to actual penetrate the endocardium, better uniform tissue contact is achieved, both beneath the surface about the temperature sensor and at the surface along the electrode.

The temperature sensing element 40 can project into the tissue at any depth desired, depending upon the tissue morphology of the individual patient and the experience and judgment of the attending physician, provided, of course, that transmural penetration of the heart wall does not occur.

Figure 6:
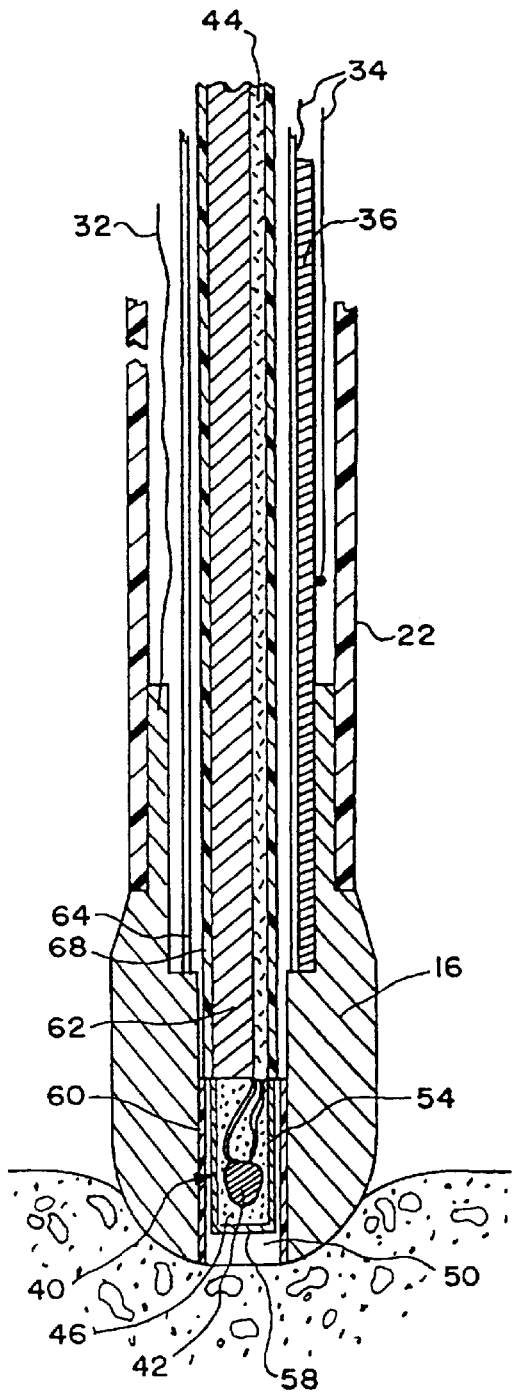
FIG. 6 is a side section view of another energy transmitting electrode that can be associated with the system shown in FIG. 1, showing a movable temperature sensing element carried within a heat conducting cap by the electrode, the sensing element being shown in its retracted position within the electrode.

In the most preferred arrangement (see FIGS. 6 and 7), the temperature sensing element 40 is movable by the physician between a retracted position within the electrode well 50 (as FIG. 6 shows) and an extended position outside the electrode well 50 and projecting into tissue (as FIG. 7 shows). In FIGS. 6 and 7, the temperature sensing element 40 includes the isothermal cap 54, which is shown to have a blunt distal end 58 (like that shown in FIG. 4). It should be appreciated that the cap 54 could alternatively have a sharpened distal end 58 (like that shown in FIG. 5).

The movable nature of the temperature sensing element 40 provides added protection against bending or fracture of the element until the moment of use. The movable element 40 can be retained in a retracted position (as shown in FIG. 6) during handling outside the body and while being deployed to the desired site within the body.

The movement of the temperature sensing element 40 can be accomplished in various ways. In the embodiment shown in FIGS. 6, 7, and 8, a stylet 62 extends through the catheter body 22 within a protective sleeve 64 (see FIGS. 6 and 7), made of, for example, polyamide or stainless steel. As FIG. 8 shows, the proximal end of the stylet 62 is attached to a control knob 66 on the handle 20 (also shown in FIG. 1). The distal end of the stylet 62 is secured by adhesive, solder, crimping, or the like to the cap 54.

As FIGS. 6 and 7 show, the thermistor wires 44 extend along the outside of the stylet 62 within the protective sleeve 64. Another sleeve 68 of electrically insulating material, like heat shrink tubing made from Teflon® or polyester material, preferably encloses the stylet 62 and wires 44 up to and around the junction between the cap 54 and the stylet 62. The added sleeve 68 holds the wires 44 tightly against the stylet 62. The added sleeve 68 also creates a smooth transition between the stylet 62 and cap 54, while also providing extra protection against electrical interference. The barrier 60 also preferably lines the interior of the well 50 to thermally and electrically insulate the cap 54 from the thermal mass of the electrode 16.

The stylet 62 can be manually or automatically advanced in various ways. In the illustrated embodiment, the stylet 62 includes helical lands 70 formed along a portion of its length (see FIG. 8). The lands 70 engage mating screw threads 82 within a stationary guide element 72 within the handle 20. Rotation of the control knob 66 by the physician rotates the stylet 62 within the guide element 72. Upon rotation in one direction, the helical lands 70 move the stylet 62 forward axially within the catheter body 22. Upon rotation in the opposite direction, the helical lands 70 move the stylet 62 rearward axially within the catheter body 22. In this way, the sensing element 40 can be incrementally moved in a controlled fashion between the retracted and extended positions.

In the illustrated and preferred embodiment, the distal cap end 58 and the distal tip of the electrode 16 are marked with a fluoroscopically dense material. In this way, the travel of the temperature sensing element 40 into the tissue can be monitored by fluoroscopy as the physician incrementally advances the element 40.

Figure 10A:
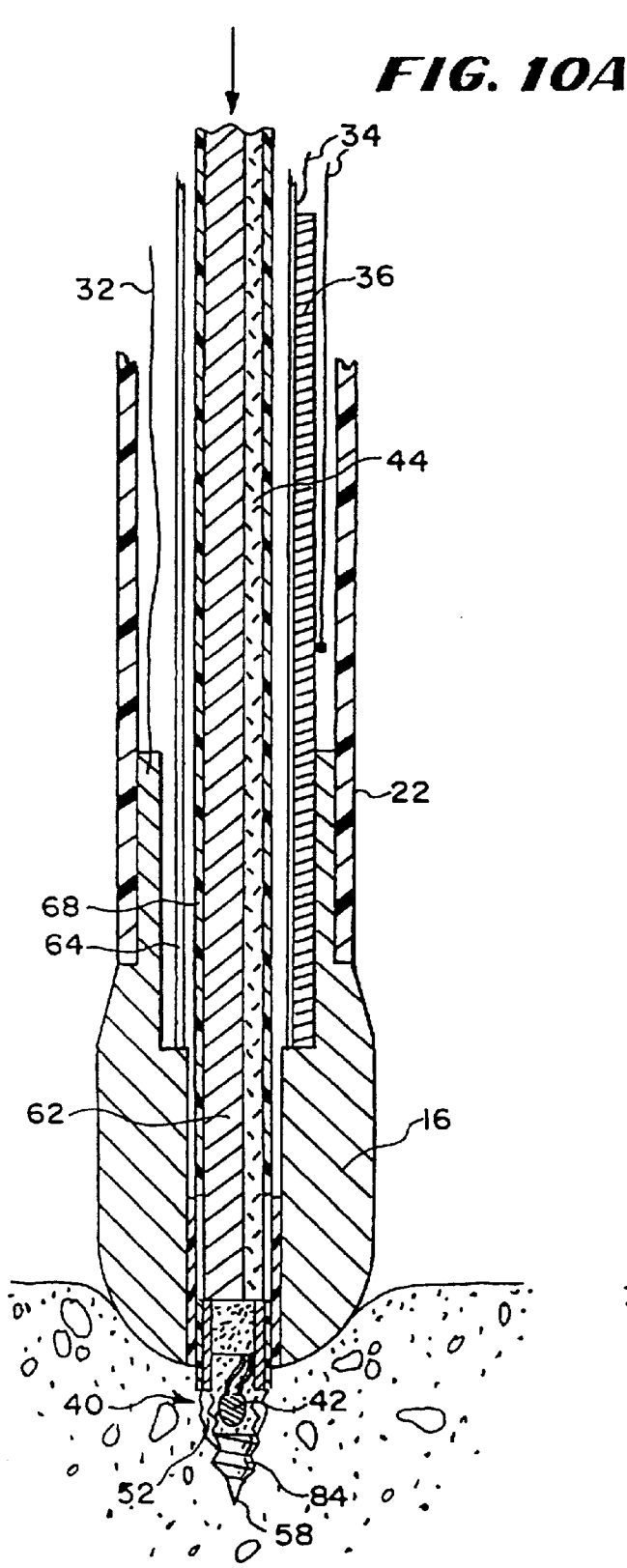
FIG. 10A is a side section view of another energy transmitting electrode that can be associated with the system shown in FIG. 1, showing an outward projecting, pointed end temperature sensing element carried within an externally threaded heat conducting cap by the electrode for sensing tissue temperature below the tissue surface.
Figure 10B:
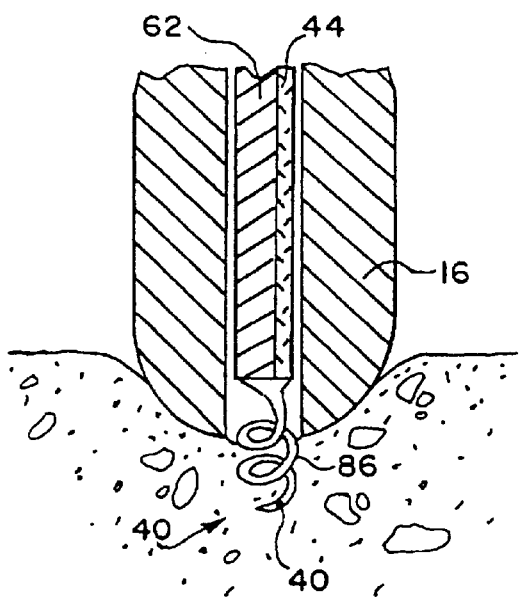
FIG. 10B is a cork-screw type carrier for the temperature sensing element that can engage tissue during advancement by rotation.
Figure 11:
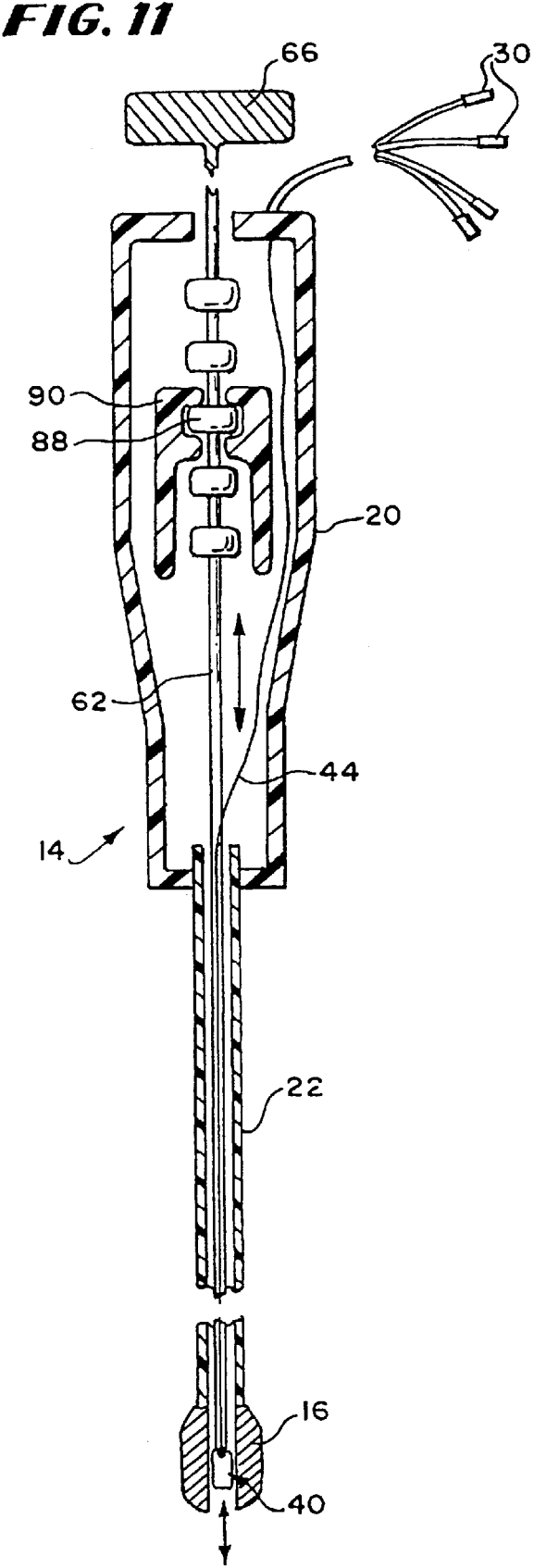
FIG. 11 is a section view of a manually, linearly movable stylet used to incrementally adjust the position of the movable temperature sensing element shown in FIGS. 6 and 7.

In another arrangement (see FIG. 10A), the distal cap end 58 can itself be threaded with helical lands 84. Upon rotational advancement of the sensing element 40 by the stylet 62, the helical lands 84 engage tissue to better anchor the element 40 for temperature sensing. Alternatively (see FIG. 10B), the stylet 62 can be attached to a carrier 86 configured as a cork-screw. Like the helical lands 84, the cork-screw carrier 86 engages tissue during rotation as the stylet 62 is advanced forward by rotation. As FIG. 10B shows, the temperature sensing element 40 is secured in thermal conductive contact with the cork-screw carrier 86 near its distal tip.

The embodiment shown in FIG. 9 includes a motor-driven mechanism 74 for advancing the stylet 62. In the illustrated embodiment, the mechanism 74 includes a feedback controller 76 electrically coupled to the temperature sensing element 40. By incrementally advancing the stylet 62, while taking instantaneous measurements of temperature condition at each increment, the feedback controller 76 moves the element 40 to seek the sub-surface tissue region where the highest temperature conditions exist. The controller 76 thereafter incrementally adjusts the position of the element 40, as necessary, to maintain it in the highest sub-surface temperature region.

Alternatively, the stylet 62 can be advanced without rotation. In this arrangement (see FIG. 11), the proximal end of the stylet 62 includes a series of ribs 88 which successively make releasable, snap-fit engagement with detent 90 in the handle 20. As the physician moves the stylet 62 in a linear (push-pull) direction, the detent 90 captures the ribs 88 one at a time, releasing the captured rib 88 in response to further linear force. Like the rotating stylet 62 shown in FIG. 8, the linear (push-pull) stylet 62 shown in FIG. 11 permits controlled, incremental movement of the sensing element 40 into and out of tissue contact.

In the embodiment shown in FIG. 12, the temperature sensing element 40 includes multiple thermocouples designated 42(1), 42(2), and 42(3). The multiple thermocouples 42(1), 42(2), and 42(3) are arranged in a housing 90 in a spaced-apart stacked relationship along the axis of the housing 90. The housing 90 can be fixed in an outwardly projecting position, as FIG. 12, or the housing 90 can be moved into an out of the projecting position in the manner of the stylet-movable cap 54 previously described (as shown in FIGS. 6 and 7).

In one embodiment (as FIG. 12 shows), the housing 90 comprises a body formed from a conventional potting compound, like silicon rubber, RTV adhesive, polyurethane, or epoxy, having a thermal conductivity less than the tissue it contacts. In the illustrated environment, where the thermal conductivity of myocardium is about 0.43 W/m K, potting compounds like silicon rubber and polyurethane material, for example, have thermal conductivities of, respectively, 0.13 W/m K and 0.026 W/m K. The relatively low thermal capacity of this material conditions the elements 42(1)/42(2)/42(3) to sense localized relative changes in the tissue temperature gradient along the length of the housing 90. The sensing of the relative temperature gradient permits the identification along the gradient of the maximum tissue temperature region for control purposes, although the temperatures sensed by the elements 42(1)/42(2)/42(3) will not directly represent actual tissue temperatures.

If a more direct correspondence between sensed and actual tissue temperatures is required, the housing 90 (see FIG. 13) can include spaced bands 92(1), 92(2), and 92(3) of thermal conductive material having thermal conductivity well above the contacted tissue, of at least 1.0 W/m K, as already described. The spaced bands 92(1), 92(2), 92(3) establish localized regions of thermal conductive contact between individual sensing element 42(1), 42(2), and 42(3)

and tissue immediately adjacent to the respective band. Thermal insulating material 94 substantially isolates the spaced bands 92(1), 92(2), and 92(3) from thermal conductive contact with each another. The thermally isolated bands 92(1), 92(2), and 92(3), each with a relatively high thermal conductivity, more accurately obtain the actual tissue temperature gradient along the length of the housing 90, than when materials with lower thermal conductivities are used.

In either embodiment, the multiple, axially stacked thermocouples 42(1), 42(2), and 42(3) allow the physician to obtain and monitor a profile of temperate conditions at different depths beneath the tissue surface. The physician can manually select for ablation control purposes the one thermocouple located in the hottest sub-surface temperature region. Alternatively, an automated control mechanism can automatically compare temperatures from all thermocouples 42(1), 42(2), and 42(3) and output the hottest sub-surface temperature for temperature control purposes.

In the embodiment shown in FIG. 14, an array of multiple, spaced-apart temperature sensing elements (designated 40(1), 40(2), and 40(3)) project from the electrode 16. Each temperature sensing element 40(1), 40(2), and 40(3) is preferably contained within an isothermal cap 54, as previously disclosed, and contain a single thermistor 42 (as FIG. 13 shows), or multiple spaced-apart thermocouples (in the manner shown in FIG. 12). The array shown in FIG. 14 allows the physician to obtain and monitor a spatial map of sub-surface temperature conditions about the electrode 16. The physician can manually select for ablation control purposes the one sensing thermistor or thermocouple 40 located in the hottest sub-surface temperature region. Alternatively, an automated control mechanism can automatically compare temperatures from all sensing elements 40(1), 40(2), and 40(3) and output the hottest sub-surface temperature for temperature control purposes. When the multiple-sensor array shown in FIG. 14 is shown, the proper orientation of the electrode 16 generally perpendicular to the tissue surface is less critical than when single-sensor embodiments are used.

II. The RF Generator

Referring back to FIG. 1, when used for cardiac ablation, the generator 12 is typically conditioned to deliver up to 150 watts of power at a radio frequency of 500 kHz. As FIG. 1 shows, the generator 12 includes a controller 78.

The controller 78 includes an input device 80 for receiving from the physician certain control parameters. One of these parameters is a maximum power value, which represents the maximum power that should be supplied to the ablation electrode 16, given its operating characteristics and the characteristics of the lesion desired.

Another one of the input parameters is the set temperature value $T_{SET}$. The set temperature value $T_{SET}$ represents the temperature the physician wants to maintain either at the surface or below the surface of the ablation site, depending upon the physician's preference and the type of temperature sensing element 40 carried by the ablation electrode 16. The set temperature value $T_{SET}$ selected depends upon the type of temperature sensing element (i.e., whether it senses surface or sub-surface temperature conditions) and the desired characteristics of the lesion. Typical therapeutic lesion characteristics are the cross-section and depth of the lesion. Typically, the set temperature $T_{SET}$ is in the range of 50 to 90 degrees C, which is safely below the temperatures at which micro explosions occur. The value of $T_{SET}$ can comprise a fixed, targeting magnitude, or the value of $T_{SET}$ can vary over time to define a set temperature curve, which can be either linear or nonlinear.

The controller 78 receives from the temperature sensing element 40 a temperature control signal $T_{CONTROL}$, which is based upon the actual instantaneous tissue temperature conditions sensed $T_M(t)$ by the sensing element 40.

The controller 78 compares the instantaneous temperature $T_M(t)$ to the set temperature value $T_{SET}$. Based upon this comparison, and taking into account the magnitude of the instantaneous power then being supplied to the ablating electrode 16, the controller 78 derives the demand power output $P_{DEMAND}$. The controller 78 can also take into account other system operating goals and criteria, like response time, steady state temperature error, and maximum temperature overshoot.

The demand power output $P_{DEMAND}$ of the controller 78 represents the magnitude of the radio frequency power that should be supplied to the ablation electrode 16 to establish or maintain the desired local temperature condition $T_{SET}$ at the ablating electrode 16, provided the demand power output is less than the maximum set power value.

The manner in which the controller 78 derives $P_{DEMAND}$ can vary. For example, it can employ proportional control principles, proportional integral derivative (PID) control principles, adaptive control, neural network, and fuzzy logic control principles. Further details of these control principle are disclosed in copending U.S. patent application Ser. No. 08/266,023, filed Jun. 27, 1994, and entitled "Tissue Heating and Ablation Systems and Methods Using Time-Variable Set Point Temperature Curves for Monitoring and Control."

The illustrated and preferred embodiments envision the use of micro-processor controlled components using digital processing to analyze information and generate feedback signals. It should be appreciated that other logic control circuits using micro-switches, AND/OR gates, invertors, and the like are equivalent to the micro-processor controlled components and techniques shown in the preferred embodiments.

Various features of the invention are set forth in the following claims.

We claim:

1. An apparatus for ablating body tissue comprising an ablation electrode having a thermal mass, the ablation electrode having a contact region for contacting tissue at a tissue surface, the ablation electrode adapted to be connected to a source of radio frequency energy to conduct radio frequency energy for transmission by the ablation electrode into the tissue surface contacting the tissue contact region, the ablation electrode including an interior well in the tissue contact region, a tissue temperature sensing assembly carried within the interior well comprising a cap made of a thermal conductive material having a thermal conductivity that is at least 1.0 W/m K, and an insulating barrier made of thermal insulating material in the interior well to substantially thermally isolate the cap from the thermal mass of the ablation electrode, the cap having a distal end enclosing at least two tissue temperature sensing elements in a spaced apart relationship in thermal conductive contact with the thermal conductive material of the cap, the distal end of the cap projecting outside the interior well and beyond the tissue contact region and into thermal conductive contact with tissue at different distances beneath the tissue surface, the thermal conductive material of the cap reaching thermal equilibrium with tissue temperature conditions without dissipation by the thermal mass of the ablation electrode.

2. An apparatus for ablating body tissue comprising an ablation electrode having a thermal mass, the ablation element having a contact region for contacting a tissue surface, the ablation electrode being adapted to be connected to a source of radio frequency ablation energy to conduct the radio frequency ablation energy for transmission by the ablation electrode into the tissue surface contacting the tissue contact region, the ablation electrode including an interior well in the tissue contact region, a tissue temperature sensing assembly carried within the interior well comprising a cap made of a thermal conductive material having a thermal conductivity that is at least 1.0 W/m K, and an insulating barrier made of thermal insulating material in the interior well to substantially thermally isolate the cap from the thermal mass of the ablation electrode, the cap having a distal end enclosing at least two tissue temperature sensing elements in a spaced apart relationship in thermal conductive contact with the thermal conductive material of the cap while being substantially isolated from electrical contact with the cap, the distal end of the cap projecting outside the interior well and beyond the tissue contact region and into thermal conductive contact with tissue at different distances beneath the tissue surface to obtain a profile of tissue temperatures beneath the tissue surface, the thermal conductive material of the cap reaching thermal equilibrium with tissue temperature conditions without dissipation by the thermal mass of the ablation electrode.

3. An apparatus according to claim 1 or 2 and further including a generator coupled to the ablation electrode for supplying radio frequency ablation energy, and a controller coupled to the tissue temperature sensing elements and the generator to control the supply of radio frequency ablation energy based, at least in part, upon tissue temperature conditions sensed by the tissue temperature sensing elements at different distances beneath the tissue surface.

4. An apparatus according to claim 1 or 2 wherein the distal end of the cap comprises a blunt surface that projects outside the interior well and into thermal conductive contact with tissue at different distances beneath the tissue surface.

5. An apparatus according to claim 4 wherein at least one of the tissue temperature sensing elements comprises a thermistor.

6. An apparatus according to claim 4 wherein at least one of the tissue temperature sensing elements comprises a thermocouple.

7. An apparatus according to claim 1 or 2 wherein the distal end of the cap comprises a sharpened point that penetrates tissue outside the interior well and makes thermal conductive contact with tissue at different distances beneath the tissue surface.

8. An apparatus according to claim 7 wherein at least one of the tissue temperature sensing elements comprises a thermistor.

9. An apparatus according to claim 7 wherein at least one of the tissue temperature sensing elements comprises a thermocouple.

10. An apparatus according to claim 1 or 2 and further including a mechanism attached to the cap to selectively move the the cap in the interior well between a first position in which the distal end of the cap and the tissue temperature sensing elements are withdrawn from thermal conductive contact with tissue beneath the the tissue surface and a second position in which the distal end of the cap and the tissue temperature sensing elements are placed into thermal conductive contact with tissue at different distances beneath the tissue surface.

11. A system according to claim 10 wherein the mechanism is configured to rotate the cap in the interior well to thereby move the distal end of the cap beyond the tissue contact region of the ablation electrode.

12. A system according to claim 10 wherein the mechanism is configured to move the distal end of the cap beyond the tissue contact region of the ablation electrode without rotation of the cap in the interior well.

13. An apparatus according to claim 1 or 2 wherein the cap includes spaced regions comprising the thermal conductive material, each spaced region being in thermal conductive contact with one of the tissue temperature sensing elements, the spaced regions being substantially isolated from thermal conductive conduct with each other and with the thermal mass of the ablation electrode.

14. An apparatus according to claim 13 wherein at least one of the regions includes a metallic material.

15. An apparatus according to claim 14 wherein the metallic material is selected from the group consisting of stainless steel, gold, silver alloy, platinum, copper, nickel, titanium, aluminum, and compositions containing stainless steel, gold, silver, platinum, copper, nickel, titanium, and aluminum.

* * * * *